(12) United States Patent
Olsen et al.

(10) Patent No.: US 6,336,918 B1
(45) Date of Patent: Jan. 8, 2002

(54) COLLECTING BAG FOR HUMAN BODY WASTES HAVING AN IMPROVED DISCHARGE MEANS

(75) Inventors: Hans Olsen, Hørsholm; Lars Bo Poulsen, Helsingør; Birthe Vestbo Andersen, Espergærde; Søren Hansen, Helsingør; Michael Hansen, Strand Børstrup, all of (DK)

(73) Assignee: Coloplast A/S, Humlebaek (DK)

( * ) Notice: Subject to any disclaimer, the term of this patent is extended or adjusted under 35 U.S.C. 154(b) by 0 days.

(21) Appl. No.: 09/572,951

(22) Filed: May 18, 2000

Related U.S. Application Data

(63) Continuation of application No. PCT/DK98/00491, filed on Nov. 13, 1998.

(30) Foreign Application Priority Data

Nov. 19, 1997 (DK) .................................................. 1314
Jun. 19, 1998 (DK) .................................................. 0805

(51) Int. Cl.[7] .............................................. A61F 5/445
(52) U.S. Cl. ....................................... 604/332; 604/355
(58) Field of Search ................................ 604/332, 355, 604/339

(56) References Cited

U.S. PATENT DOCUMENTS

| | | | |
|---|---|---|---|
| 2,520,831 A | 8/1950 | Chincholl | 128/283 |
| 3,507,282 A | 4/1970 | Burding | 128/283 |
| 3,690,320 A | 9/1972 | Riely | 128/283 |
| 4,988,343 A | 1/1991 | Ballan | 604/332 |
| 5,125,133 A | 6/1992 | Morrison | 24/30.5 R |
| 5,951,533 A | * 9/1999 | Freeman | 604/338 |
| 5,968,024 A | 10/1999 | Freeman | 604/334 |

FOREIGN PATENT DOCUMENTS

| | | |
|---|---|---|
| DE | 27 22 445 | 11/1978 |
| GB | 2 000 683 | 1/1979 |
| GB | 2 268 065 | 1/1994 |
| WO | 96/19164 | 6/1996 |

* cited by examiner

Primary Examiner—John G. Weiss
Assistant Examiner—Michael Bogart
(74) Attorney, Agent, or Firm—Jacobson Holman, PLLC

(57) ABSTRACT

A collecting bag comprising a bag member formed by two film blanks with joined edges, an inlet opening being provided in one of the film blanks surrounded by connecting elements for connection of the bag to a body orifice. The bag is emptied through a narrowed, elongated discharge portion ending in a discharge opening. A closure device provided at the discharge portion for bringing the bag from an open to a closed position of use includes a first closure means at the proximal or distal end of the discharge portion and a second closure means. The closure device is arranged for opening and closing of the bag in two distinct stages by successive operation of the first and second closure means.

32 Claims, 6 Drawing Sheets

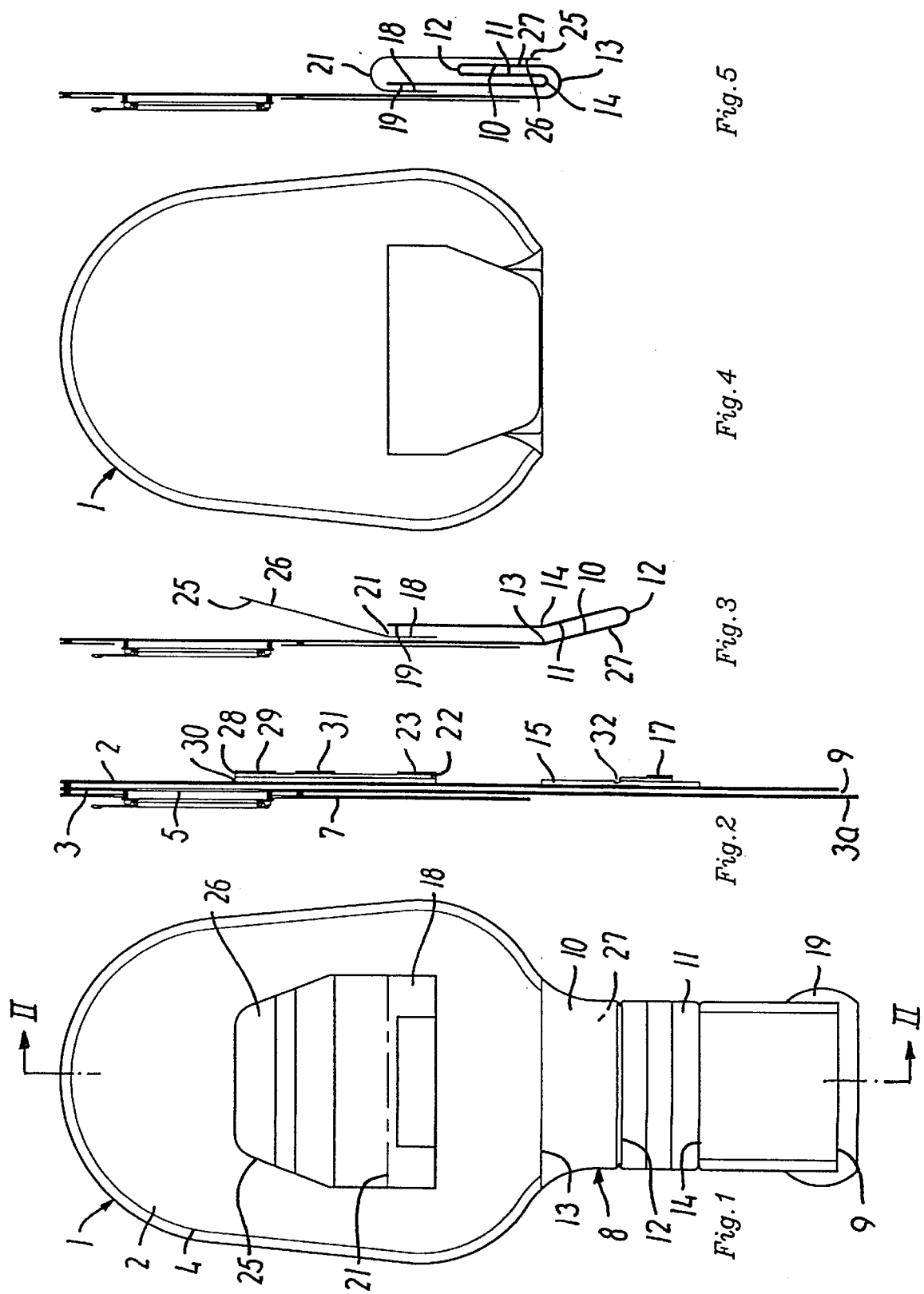

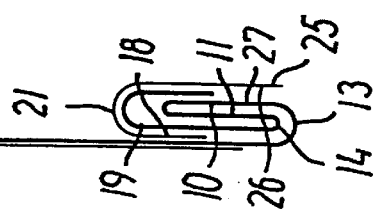
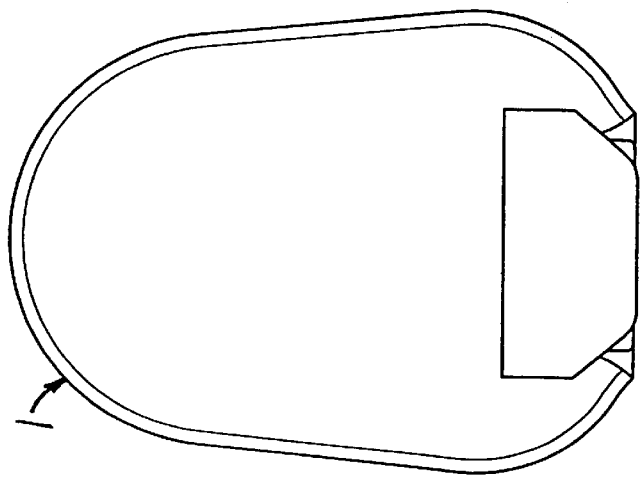
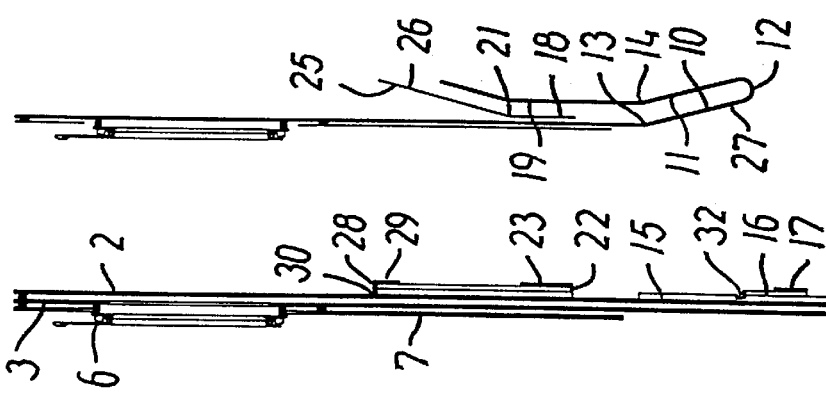
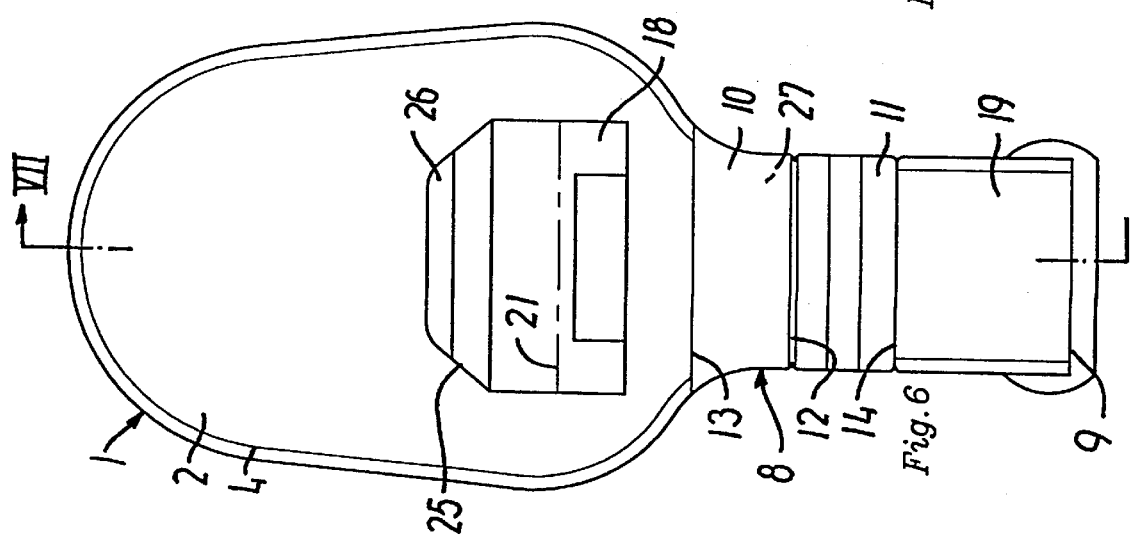

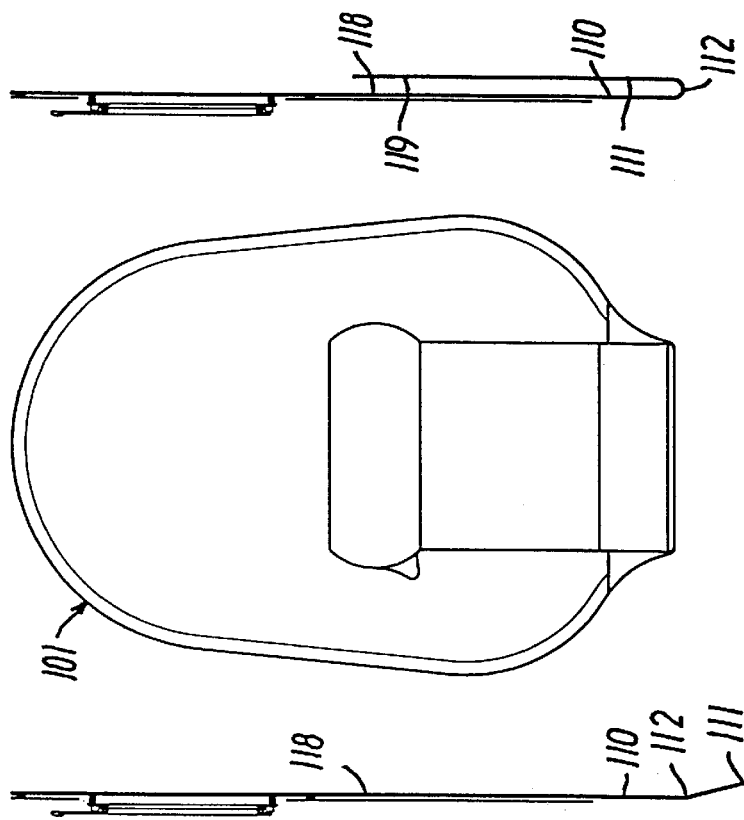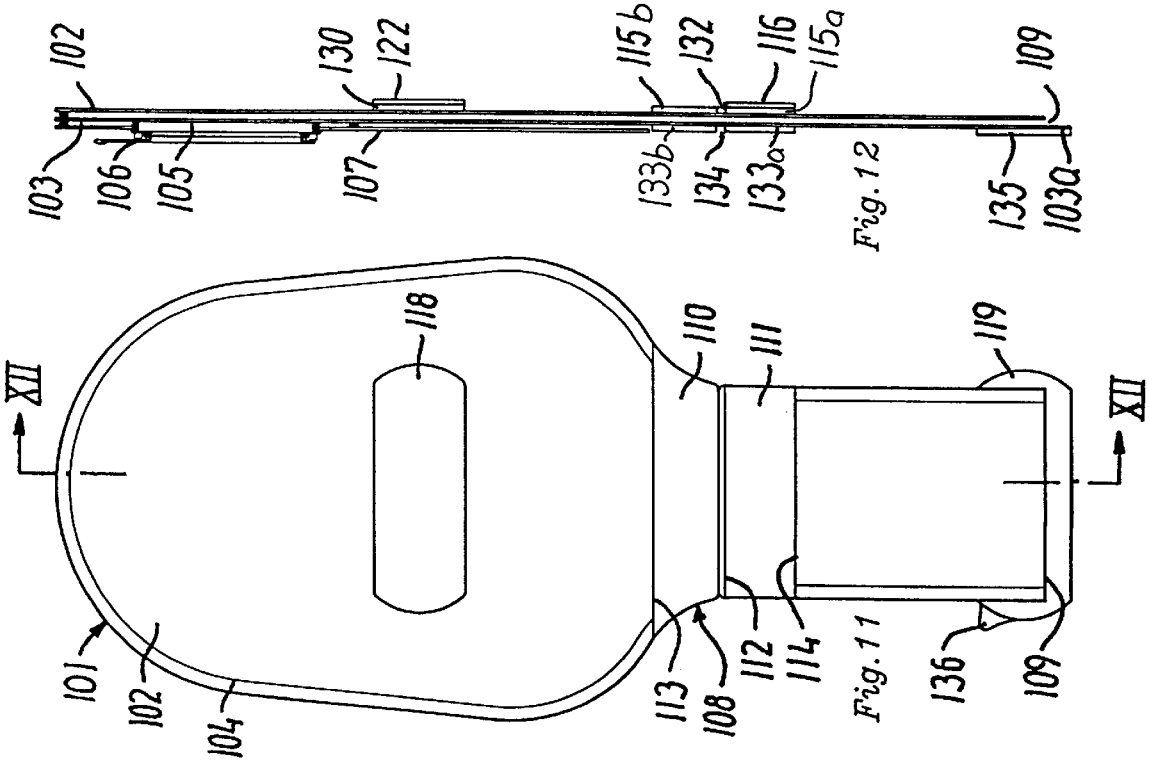

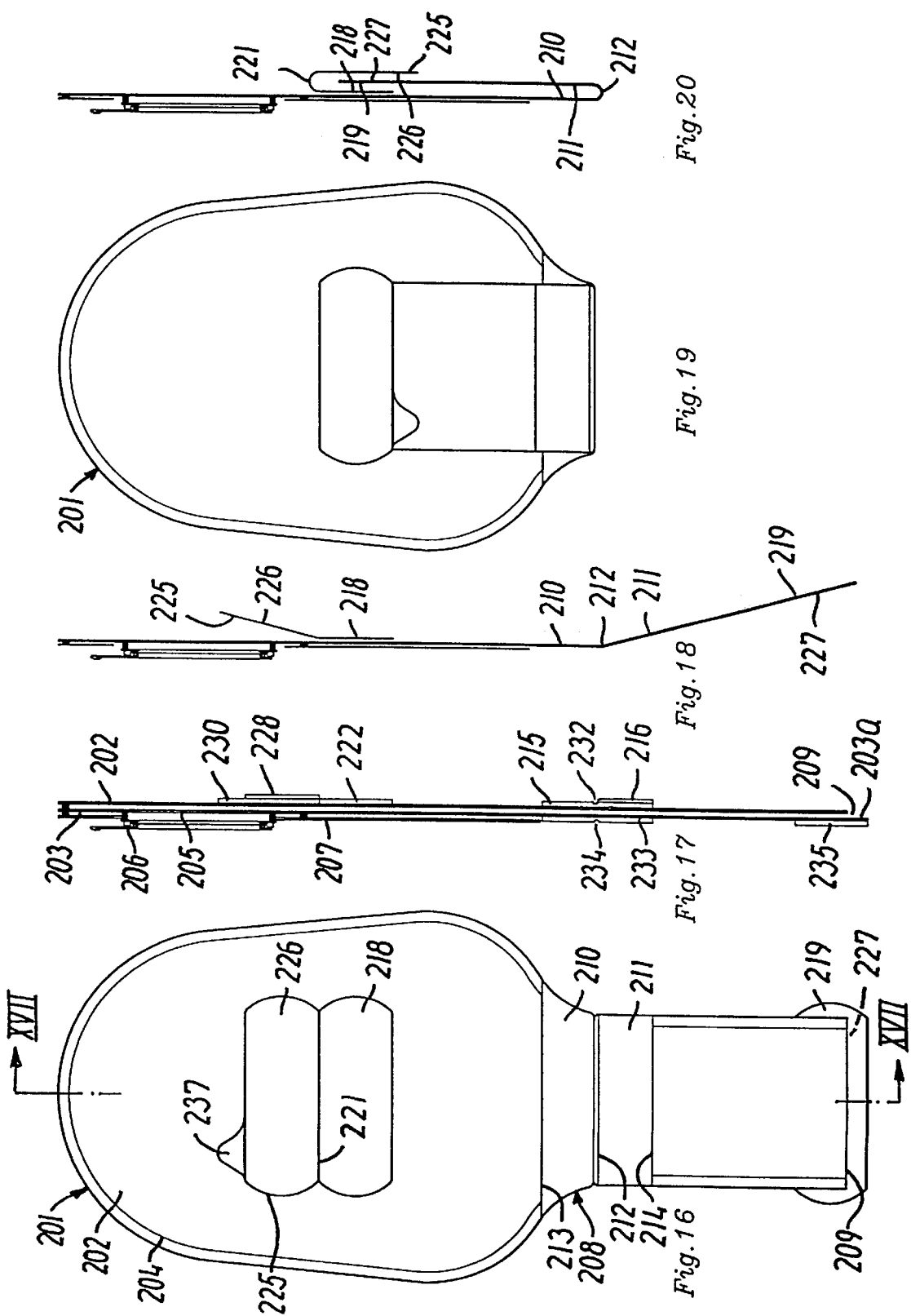

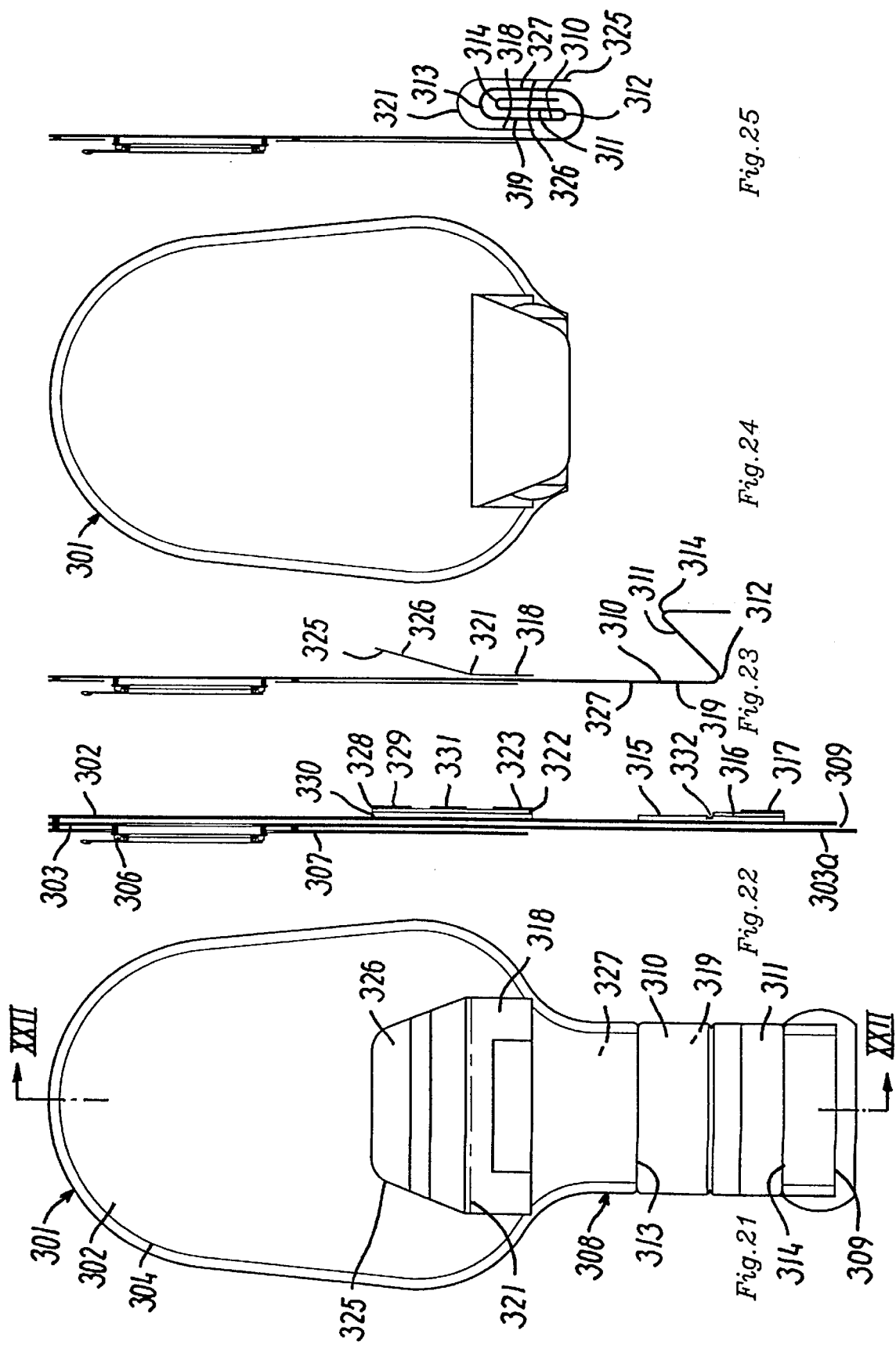

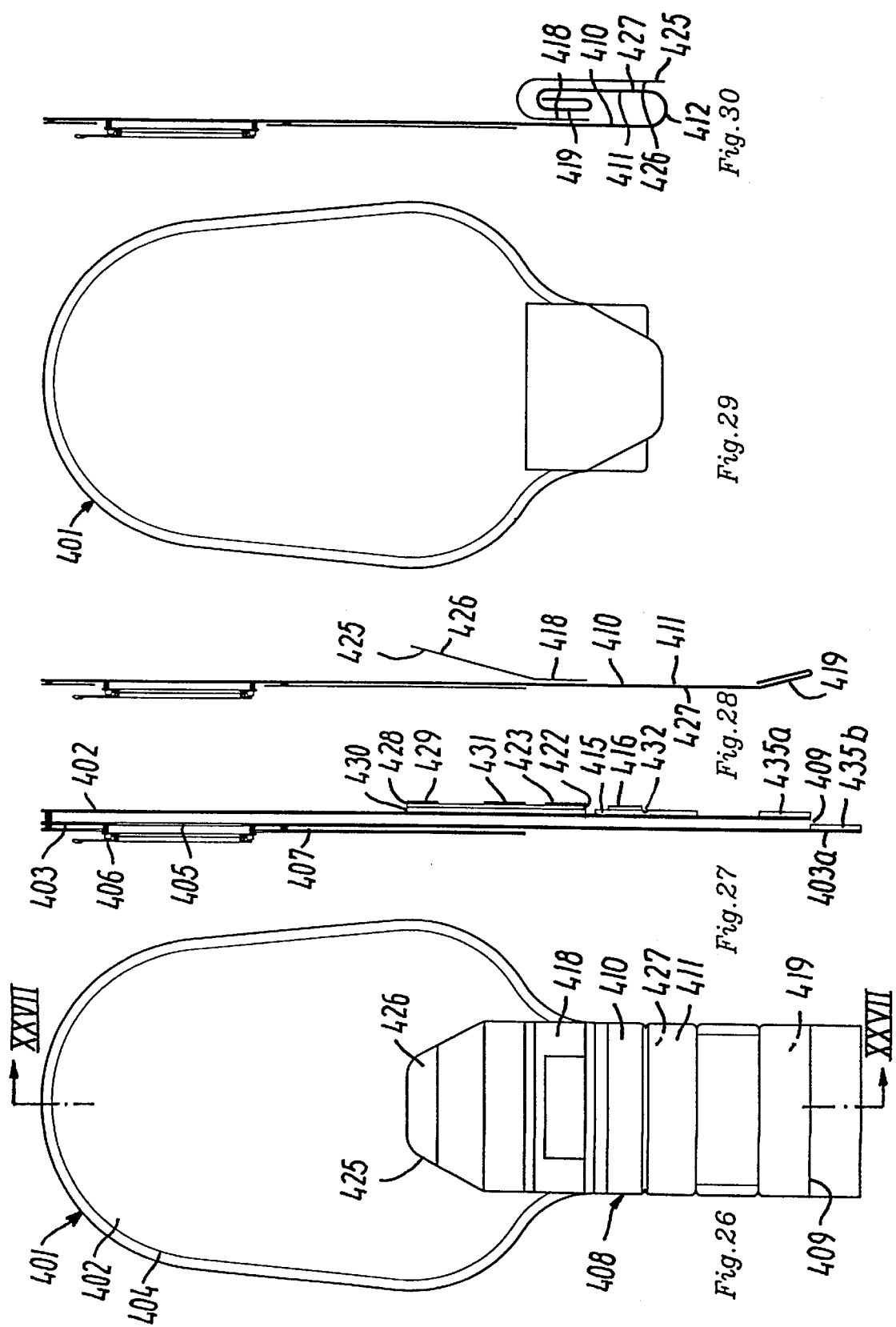

COLLECTING BAG FOR HUMAN BODY WASTES HAVING AN IMPROVED DISCHARGE MEANS

CROSS-REFERENCE TO RELATED APPLICATIONS

The present application is a continuation application of PCT/DK98/00491, filed Nov. 13, 1998.

BACKGROUND OF THE INVENTION

The invention relates to a collecting bag for human body wastes comprising a bag member formed by two film blanks with joined edges, an inlet opening provided in one of said film blanks, connecting elements surrounding said inlet opening for connection of the bag to a body orifice, a narrowed, elongated discharge portion starting at a proximal end at a distance from the inlet opening and extending between two end sections of said film blanks to a distal end, a discharge opening formed in said discharge portion in the vicinity of said distal end, and a closure device being provided for bringing the discharge portion from an open discharge position to a closed position of use, the closure device comprising a first and a second closure means, both of which are activated in said position of use.

These types of drainable collecting bags are often used as ostomy bags. In the case of ileostomy patients and colostomy patients with uncontrolled release of feces of a more or less fluid consistence, the collecting bag has to be emptied rather frequently, and the closure device thus has to be easy to open and reclose after emptying and at the same time provide a reliable and tight seal in operation, i.e., between emptyings.

Several different designs of closure devices have been developed and are generally known.

For example, U.S. Pat. No. 5,125,133 discloses a clamp type closure device comprising a blade like wedge member and a U-shaped trough member which are hingedly connected at one end and are clamped together around the discharge portion of the collecting bag.

Another type of closure device is shown in eg. DK-B-153 206 (corresponding to U.S. Pat. No. 4,988,343) and published international application No. WO96/19164, in which the discharge portion is rolled up on a clip fastened to one of the film blanks, near the discharge opening.

Although closure devices of the clip or clamp category have proven effective over the years, there are a number of inconveniences connected with such a closure.

As a consequence of their construction, these known closure devices suffer from the drawback that they are rather bulky and may thus be seen under the user's clothing and are often made from a stiff material, or a softer material having stiff reinforcing elements, implying a risk of irritating or chafing the skin. As a consequence, the user will not experience the desired discretion and comfort of wear, and the closure device will render the collecting bag unpleasant to use.

In order to alleviate these problems, another category of closure devices has been developed and is for instance shown in GB patent applications Nos. 2 268 065 and 2 000 683, in which strips of the interlocking-elements type, such as Velcro (registered trademark), are placed on each of the film blanks of the discharge portion and which after rolling or folding the discharge portion tightly are brought into contact with each other.

A common drawback in both of these categories of known closure devices is, however, that when opening the closure in order to empty the bag, there is a risk that the contents of the bag will flow out of the discharge opening beyond the user's control, in particular if the bag is filled almost to capacity and/or flatus has gathered in the bag and the closure device is thus under pressure.

U.S. Pat. No. 2,520,831 discloses a collecting bag in which a clamp holds the folded distal end of the discharge portion together in the closed position of use of the bag. In the position of use, the folded discharge portion is accommodated in a pouch provided at the proximal end of the discharge portion, the pouch being closed by means of a zipper-like slide fastener. Due to the structure of the elements of the closure device, opening and closing of the bag require some dexterity, e.g., the, discharge portion has to be held manually within the pouch when activating the slide fastener and has to be withdrawn from the pouch in order to empty the bag. In addition to the bulkiness of the clamp type closure discussed above, the use of a slide fastener renders the manufacture of the closure device expensive and cumbersome, especially as the slide fastener has to be air-tight in order to prevent escape of odor from the discharge portion.

SUMMARY OF THE INVENTION

The object of the present invention is to improve a collecting bag of the kind mentioned in the introduction with respect to ease of operation, security against leakage and manufacturing conditions.

For achieving this, a collecting bag according to the invention is provided, said collecting bag comprising a bag member formed by two film blanks with joined edges, an inlet opening provided in one of said film blanks, connecting elements surrounding said inlet opening for connection of the bag to a body orifice, a narrowed, elongated discharge portion starting at a proximal end at a distance from the inlet opening and extending between two end sections of said film blanks to a distal end, a discharge opening formed in said discharge portion in the vicinity of said distal end, and a closure device being provided for bringing the discharge portion from an open discharge position to a closed position of use, the closure device comprising a first and a second closure means, both of which are activated in said position of use, wherein said closure device is arranged for opening and closing of the bag by successive operation of said first and second closure means in two distinct stages separated an intermediate position of the discharge portion, in which only the first closure means is activated, the first closure means comprises a first pair of contact surfaces between a first folding line and a second folding line and the first folding line and a limiting line, respectively, said contact surfaces being brought into contact by folding the discharge portion along said first folding line and are held in this position in the intermediate position and the position of use, and said contact surfaces of said first pair are provided on a carrier plate or carrier plates fastened to one of the film blanks.

By carrying out the opening of the bag in two distinct stages, namely a first stage consisting in opening the second closure means and subsequently directing the discharge portion into the correct position over a toilet or the like in the intermediate position of the bag, and a second stage in which the first closure means is opened simply by releasing the contact between the contact surfaces of the first pair, a very controlled discharge of the bag contents is achieved. Moreover, an improved safety against leakage during the use of the bag is obtained by the provision of the carrier plate or plates. Eventually, rinsing of the discharge portion after emptying of the bag is made more secure as this operation may be carried out in the intermediate position of the bag, ie., when the first closure means is activated and thus prevents newly discharged body wastes from soiling the discharge opening again. In comparison with the collecting bag of U.S. Pat. No. 2,520,831, the bag according to the invention provides for an easier operation requiring less dexterity and furthermore, the use of pre-defined contact surfaces makes the activating/deactivating order of the closing/opening stages logical and obvious to the user. At the same time, the collecting bag according to the invention offers an improved security against leakage, as the first closure means is capable of holding the bag closed as the second closure means only provides an additional protection against leakage.

In an advantageous embodiment, at least one of the contact surfaces of said first pair comprises a layer of adhesive capable of repeated adhesion. By this design, a very low thickness of the collecting bag in the position of use is obtained thus rendering the collecting bag almost unnoticeable under the wearer's clothes.

With a view to optional design of the closure device, the first closure means may either be provided at the proximal end of the discharge portion, or, in an alternative embodiment, in the vicinity of the distal end of the discharge portion.

A particularly advantageous design of the collecting bag is obtained in combination with an embodiment, in which the second closure means comprises a second pair of contact surfaces, in which said contact surfaces are brought into contact and are held in this position in the position of use of the bag and in which at least one of the contact surfaces is provided on a carrier plate. Preferably, at least one of the contact surfaces of said second pair comprises a layer of adhesive capable of repeated adhesion.

With this design, a particularly flat collecting bag is obtained and the same time, it is possible to provide the discharge portion with a considerable length in comparison to known bags, which facilitates the control of the discharge portion and the emptying of the bag even further.

In a further embodiment, the collecting bag according to the invention is characterized in that the other contact surface of said second pair at least partly is provided on the same film blank as said one contact surface of said second pair at an end zone thereof; and that a flap is provided in connection with said one contact surface of said second pair, said flap being foldable along a third folding line and being provided with a layer of adhesive capable of repeated adhesion and constituting one contact surface of a third pair, the other contact surface of said third pair being provided on the opposite film blank of the discharge portion.

The other contact surface of said third pair is preferably provided opposite the contact surface of said first pair situated between the first and second folding lines, and said flap has a length substantially corresponding to the distance between the third folding line and the proximal end of the discharge portion, the discharge portion being folded onto the bag member along the second folding line and the limiting line in the position of use of the bag.

By this embodiment, a particularly compact and fluid tight design is provided, due to the fact that the contact between the third pair of contact surfaces contributes to an additional tightening of the contact between the first pair of contact surfaces as the contents of the bag exert a pressure on the first closure means.

In a further development of the above-mentioned alternative embodiment, said one contact surface of the second pair is provided at the proximal end of the discharge portion or at a section of the bag member adjacent the discharge portion.

BRIEF DESCRIPTION OF THE DRAWINGS

In the following the invention will be described in further detail with reference to the schematic drawings, in which FIG. 1 shows a plan view of a first embodiment of a collecting bag according to the invention, seen from the side intended to face away from the user and in the fully open position;

FIG. 2 shows a longitudinal section of the collecting bag along the line II—II in FIG. 1;

FIG. 3 is a schematic side view diagram of the collecting bag in an intermediate position showing only relevant parts of the bag;

FIG. 4 is a view corresponding to FIG. 1 in the fully closed position of the bag;

FIG. 5 is a diagram corresponding to FIG. 3 of the collecting bag in the fully closed position;

FIG. 6 shows a plan view of a second embodiment of a collecting bag according to the invention, seen from the side intended to face away from the user and in the fully open position;

FIG. 7 shows a longitudinal section of the collecting bag along the line VII—VII in FIG. 6;

FIG. 8 is a schematic side view diagram of the collecting bag in an intermediate position showing only relevant parts of the bag;

FIG. 9 is a view corresponding to FIG. 6 in the fully closed position of the bag;

FIG. 10 is a diagram corresponding to FIG. 8 of the collecting bag in the fully closed position;

FIG. 11 shows a plan view of a third embodiment of a collecting bag according to the invention, seen from the side intended to face away from the user and in the fully open position;

FIG. 12 shows a longitudinal section of the collecting bag along the line XII—XII in FIG. 11;

FIG. 13 is a schematic side view diagram of the collecting bag showing only relevant parts of the bag;

FIG. 14 is a view corresponding to FIG. 11 in the fully closed position of the bag;

FIG. 15 is a diagram corresponding to FIG. 13 of the collecting bag in the fully closed position;

FIG. 16 shows a plan view of a fourth embodiment of a collecting bag according to the invention, seen from the side intended to face away from the user and in the fully open position;

FIG. 17 shows a longitudinal section of the collecting bag along the line XVII—XVII in FIG. 16;

FIG. 18 is a schematic side view diagram of the collecting bag showing only relevant parts of the bag;

FIG. 19 is a view corresponding to FIG. 16 in the fully closed position of the bag;

FIG. 20 is a diagram corresponding to FIG. 18 of the collecting bag in the fully closed position;

FIG. 21 shows a plan view of a fifth embodiment of a collecting bag according to the invention, seen from the side intended to face away from the user and in the fully open position;

FIG. 22 shows a longitudinal section of the collecting bag along the line XXII—XXII in FIG. 21;

FIG. 23 is a schematic side view diagram of the collecting bag showing only relevant parts of the bag;

FIG. 24 is a view corresponding to FIG. 21 in the fully closed position of the bag;

FIG. 25 is a diagram corresponding to FIG. 23 of the collecting bag in the fully closed position;

FIG. 26 shows a plan view of a sixth embodiment of a collecting bag according to the invention, seen from the side intended to face away from the user and in the fully open position;

FIG. 27 shows a longitudinal section of the collecting bag along the line XXVII—XXVII in FIG. 26;

FIG. 28 is a schematic side view diagram of the collecting bag showing only relevant parts of the bag;

FIG. 29 is a view corresponding to FIG. 26 in the fully closed position of the bag;

FIG. 30 is a diagram corresponding to FIG. 28 of the collecting bag in the fully closed position.

In FIGS. 2, 7, 12, 17, 22 and 27 some sectional areas are indicated by fully drawn lines in order not to impede the clear reading of the drawings.

DETAILED DESCRIPTION OF THE INVENTION

The collecting bag shown in the drawings is designed as an ostomy bag of a generally known and common type. With reference to the first embodiment shown in FIGS. 1 to 5 of the drawings, the collecting bag comprises a bag member 1 formed by two film blanks 2,3 which are joined along their edges by means of a seam 4 made by welding or in any other convenient manner. The film blanks may be made from any suitable flexible plastic sheet or foil material.

In the film blank 3 which in use is intended to face the user and thus forms the back wall of the bag, an inlet opening 5 is provided which in a manner known per se is surrounded by connecting elements 6 for connection of the bag to a body orifice, ie. in this case an intestinal orifice in the form of a so-called stoma in the user's abdominal wall.

As most clearly seen in FIG. 2 a comfort layer 7 of another material than the one used for the film blanks is provided on the back film blank 3.

At a distance from the inlet opening 5, the bag is designed with a narrowed, elongated discharge portion 8 starting at a proximal or neck end and extending to a distal or terminal end. The discharge portion 8 is formed by two end sections of the film blanks 2,3 and is likewise joined along its side edges.

In the vicinity of the distal end of the discharge portion, a discharge opening 9 through which the bag may be emptied of its contents is formed by the slit between the end edges of the two film blanks 2,3.

In order to bring the bag from the open or discharge position shown in FIGS. 1 and 2 to a position of use, in which the bag is closed, the collecting bag comprises a closure device which will be described in the following.

The closure device comprises a first closure means provided at the proximal end of the discharge portion 8 and comprises a first pair of contact surfaces 10, 11, of which one extends from a first folding line 12 to a second folding line 13, and the other between the first folding line 12 and limiting line 14. The one contact surface 10 is entirely provided on a carrier plate 15 which is fastened to the front film blank 2. The carrier plate 15 extends further past the first folding line 12 in the direction towards the discharge opening 9. Here, on the other contact surface 11, the carrier plate is covered by a layer of adhesive 16 which is capable of repeated adhesion and is preferably washable. The carrier plate 15 itself is made from a foam material but may also be made from any other suitable material, such as a plastic or a fiber material, and contributes to the tight seal of the closure.

It is noted that the layer of adhesive 16 on the other contact surface 11 in the embodiment shown is partly covered by a cover layer 17 in order to facilitate the subsequent release of the adhesive contact. In order to obtain optimum function of the closure means, the size and position of the layer of adhesive 16 and/or the cover layer 17 may be varied, just as the strength of the adhesive may be varied. Furthermore, it should be noted that the layer of adhesive 16 could as well have been provided on the contact surface 10 between the first and second folding lines 12,13, or on both of these surfaces. By providing the layer of adhesive only on the contact surface 10, cleaning of the discharge portion is facilitated as it is possible to squeeze and rinse the discharge portion 8 all the way from the distal end to the first folding line 12 without coming into contact with the adhesive layer.

Following this first closing stage, after which the bag is in an intermediate position, the distal end of the discharge portion 8 is closed by means of a second closure means.

The second closure means comprises two contact surfaces 18,19 of a second pair, of which one 18 in this design is provided on a flap element fastened to the front film blank 2 in a lower portion up to a third folding line 21. The upper portion of the flap element is formed as a flap 25. The function of the flap 25 will be described further on. The contact surface 18 extends from the end edge of the flap element facing the discharge portion 8 up to the third folding line 21 which is placed at a distance from the first folding line 12 substantially corresponding to the distance between the first folding line 12 and the distal end of the discharge portion 8. At the distal end, the other contact surface 19 of the second pair is provided, partly on the front film blank 2, partly on an extended portion 3a of the back film blank 3 shown most clearly in FIG. 2.

In the position of the bag shown in FIG. 3, the two contact surfaces 18,19 of the second pair are brought into contact with each other and are held in this position by an adhesive layer 22 on the contact surface 18 on the flap element. A cover layer 23 on the contact surface 18 provides a substantially U-shaped adhesive surface in order to facilitate the subsequent release of the adhesive contact. Just as the layer of adhesive 16 on the first pair of contact surfaces, the adhesive layer 22 is capable of repeated adhesion and may also be washable.

In this position of the discharge portion 8, the collecting bag is in principle fully closed and the contents of the bag are prevented from entering into the distal part of the discharge portion 8 by means of the first closure means and an additional protection against leakage is thus provided by the second closure means. It is noted that the discharge opening 9 is covered as the extended portion 3a of the back film blank 3 overlies the opening.

As an alternative, the discharge portion 8 of a second embodiment shown in FIGS. 6 to 10, in which elements having the same of analogous function bear the same reference numerals as in the first embodiment, may have a length between the first folding line 12 and its distal end which exceeds the distance between the first folding line 12 and the third folding line 21. In this 15 case, the bag member contact surface 18 of the second pair is provided on the flap member and extends beyond the third folding line 21 further on to the flap 25 constituting the upper part of the flap element. It is noted that the surface 18 on the lower side of the third folding line 21 is not covered by the adhesive layer 22 or alternatively that this surface 18 is partly covered by a cover layer 23.

From the position shown in FIGS. 3 and 8, the discharge portion 8 is in these embodiments again folded on to the bag member 1 along the second folding line 13 and the limiting line 14 which in this position overlies the second folding line 13. Subsequently, the flap 25 is folded along the third folding line 21 so that a contact surface 26 on the flap 25 is brought into contact with another contact surface 27 constituting the other part of a third pair positioned on the back film blank 3 opposite the contact surface 10 of the first pair situated between the first and second folding lines 12, 13 on the front film blank 2. To this end, the contact surface 26 on the flap 25 is covered by a layer of adhesive 28 which is capable of repeated adhesion and which may be washable. A cover layer 29 covering the outermost part of the flap 25 provides for easier opening of the collecting bag as the flap 25 may be simply lifted in order to release the contact between the contact surfaces 26, 27. As shown in FIGS. 2 and 7, the adhesive layers 22 and 28 may be formed integrally on a carrier plate 30 extending throughout the flap element and which may be made from foam, plastic or fiber material. In order to further facilitate the lifting of the flap 25, a cover layer 31 covers the area of the flap below the contact surface 26 in the first embodiment. The same considerations regarding the size and position of the layers of adhesive and the cover layers, and the strength of the adhesive used, apply to the second and third pairs of contact surfaces.

It is noted that in the embodiment shown in FIGS. 6 to 10 the distal part of the discharge portion 8 is folded along a line opposite the third folding line 21 in the closed position of the bag. This provides for an additional security against leakage and the possibility of designing the discharge portion even longer than described in the afore-going.

The collecting bag is now in the position of use shown in FIGS. 4 and 5, and 9 and 10, respectively. As the discharge portion 8 is entirely folded on to the bag member 1, it does not at all add to the outer contour of the bag member, thus providing a very compact design of the collecting bag. It is also noted that during operation of the bag, when the contents exert a pressure on the first closure means, the contact between the first pair of contact surfaces 10,11 is tightened additionally from the contact between the contact surface 26 on the flap 25 and the other contact surface 27 on the discharge portion 8 itself.

When the collecting bag has been in use for some time and is at least partly filled, the bag is opened in a series of operations.

First, the adhesive contact between the third pair of contact surfaces 26,27 is released by lifting the flap 25 and unfolding it along the third folding line 21. The second closure means is now deactivated by pulling said one contact surface 19 of the second pair on the distal end of the discharge portion 8 out of contact with the other contact surface 18 on the flap element. Subsequently, the discharge portion 8 is unfolded and an intermediate position has been reached. It is noted that the contents of the bag are still prevented from flowing out by means of the first closure means which is still active. Only when the distal part of the discharge portion 8 has been directed into a suitable position, eg., over a toilet, the first closure means is deactivated by a pull in the distal end of the discharge portion, whereby the bag assumes its open position shown in FIGS. 1 and 6, respectively, and its contents are allowed to flow out of the bag.

Subsequently, the user may squeeze the remaining contents out of the bag by stroking or massaging movements in the direction towards the discharge opening 9. When the bag has been emptied, the discharge portion 8 may be thoroughly rinsed.

Eventually, the collecting bag may be closed by following the procedure described in the above.

In FIGS. 11 to 15 a somewhat simplified, third embodiment of the collecting bag according to the invention is shown. Elements having the same or analogous function as described in connection with the embodiment shown in FIGS. 1 to 5 bear reference numerals where 100 has been added to the reference numerals of the previous embodiment. Only the elements relevant to the closure device of the bag will be described.

The first closure means comprises two contact surfaces 110,111 which in this embodiment are provided on two separate carrier plates 115a and 115b having a spacing 132 between them extending substantially along a first folding line 112. The contact surface 111 extending between the first folding line 112 and a limiting line 114 is covered by a layer of adhesive 116 of the same type as mentioned in connection with the previous embodiment. The size and position of the layer of adhesive 116 may be varied as described in the above, just as a cover layer may be used and the strength of the adhesive may be varied. Opposite the carrier plates 115a and 115b, two supporting plates 133a and 133b are fastened to the back film blank 103. In order to facilitate the folding of the discharge portion 108 a spacing 134 is provided opposite the first folding line 112. Of course, both sets of plates 115a, 115b and 133a, 133b could be designed as a common carrier plate and supporting plate, respectively, with a notch along/opposite the first folding line.

The second closure means comprises one contact surface 118 provided on the bag member 101 and a layer of adhesive 122 placed on a carrier plate 130 is intended for adhesive contact with another contact surface 119 at the distal end of the discharge portion 108. The other contact surface 119 is provided on an extension 103a of the back film blank 103, said extension 103a being in turn supported by a supporting film element 135, which may be made from the same material as the film blanks 102,103.

The supporting film element 135 has a shape substantially corresponding to the contact surface 118 on the bag member 101, and is in the embodiment shown provided with an ear 136 in order to facilitate the subsequent release of the contact between the contact surfaces 118,119 of this second pair. As is apparent from these Figures, the discharge opening 109 will be covered by the extension 103a of the back film blank 103 in the closed position of the bag, ie., after the contact surfaces 110,111 and the second pair of contact surfaces 118,119 have been brought into contact with each other and are held in this position by the adhesive layers 116 and 122, respectively.

Opening of the collecting bag with a view to emptying is carried out by releasing the second closure means by lifting the ear 136 so that the contact between the contact surfaces 118 and 119 is disrupted. In this position, the discharge portion 108 and thus the discharge opening 109 may be directed into the desired position, following which the first closure means is released by a pull in the distal end of the discharge portion.

A still further, fourth embodiment is shown in FIGS. 16 to 20 of the drawings. The first closure means is identical to the one described in connection with the embodiment of FIGS. 11 to 15 and elements of the same and analogous function bear the same reference numerals added 100 to the ones described in connection with this embodiment.

As before, the second closure means comprises two contact surfaces 218 and 219. The contact surface 218 is provided with a layer of adhesive 222. In addition, a contact surface 226 of a third pair is provided on a flap 225 which is covered with an adhesive layer 228 applied to a carrier plate 230. Upon folding of the discharge portion 208 along the first folding line 212, the first pair of contact surfaces 210,211 are being brought into contact with each other and the contact surface 219 into contact with the contact surface 218. Following this operation, the flap 225 is folded along a third folding line 221 and the contact surface 226 is thus brought into contact with the other contact surface 227 of the third pair, which is situated on the back film blank 203 opposite the other contact surface 219 of the second pair.

In order to open the bag, the flap 225 is lifted in an ear 237 and unfolded, following which the second and then the first closure means may be deactivated as described in the above.

In the alternative, fifth embodiment shown in FIGS. 21 to 25, the collecting bag is of substantially the same design as in the embodiment described in connection with FIGS. 1 to 5. Elements having the same or analogous function as in this embodiment bear reference numerals where 300 has been added to the reference numerals of this previous embodiment. Only the elements relevant to the closure device of the collecting bag will be described in detail.

The first closure means is in this embodiment positioned in the vicinity of the distal end of the discharge portion and is provided in the form of a first pair of contact surfaces 310,311. One of the contact surfaces 310 is provided on a carrier plate 315 extending between a first folding line 312 and a second folding line 313. The other contact surface 311 is provided on another part of the carrier plate 315 and extends from the first folding line 312 to a limiting line 314 situated at a distance from the discharge opening 309 and is partly covered by a layer of adhesive 316 which may be of the same type as mentioned in connection with the previous embodiments. In order to ease the folding operation, the carrier plate 315 is provided with a notch 332 substantially extending along the first folding line 312, or the contact surfaces 310,311 may be provided on separate carrier plates with a spacing between them. As described in connection with the first embodiment, the size and position of the layer of adhesive 316 and/or the cover layer 317 may be varied as well as the strength of the adhesive. Furthermore, the layer of adhesive could as well be provided on the other contact surface 310 or on both of the surfaces 310,311.

The second closure means comprises one contact surface 318 of a second pair provided in the transition between the discharge portion 308 and the bag member 301. The contact surface 318 is provided with a layer of adhesive 322 intended for adhesive contact with the other contact surface 319 on the opposite film blank. As may be seen from the Figure, said one contact surface 318 of the second pair is positioned in such a way that the distance between the distal edge of this contact surface 318 and the second folding line 313 is approximately the same as the extension of the contact surfaces 310,311 of the first pair, ie., the distance between the first and second folding lines 312,313 and the first folding line 312 and the limiting line 314, respectively.

In this manner, the discharge portion may be folded three times, first along the first folding line 312 and then along the second folding line 313 and the limiting line 314 and subsequently one more round until the contact surface 319 has been brought into contact with the contact surface 318 and the second closure means has been activated.

Following this operation, the flap 325 is folded along a third folding line 321 and the contact surface 326 covered by a layer of adhesive 328 is brought into contact with the other surface 327 of the third pair of contact surfaces and the position of use shown in FIGS. 24 and 25 is obtained. It will be noted that the two contact surfaces 319, 327 on the discharge portion 308 are positioned adjacent each other. As shown in FIG. 22, the adhesive layers 322 and 328 may be formed integrally on a carrier plate 330 extending throughout the flap element and may be made from foam, plastic or fiber material. In order to facilitate the lifting of the flap 325, the adhesive layers 322 and 328 may be partly covered by cover layers 323, 329 and 331.

In order to open the bag, the flap 325 is lifted and unfolded, following which the second closure means is deactivated. The discharge portion 308 may now be unfolded until an intermediate position has been reached. By a pull in the distal end of the discharge portion 308, the bag is brought to its open or discharge position and the contents of the bag are allowed to flow out through the discharge opening 309.

In the alternative, sixth embodiment shown in FIGS. 26 to 30, the collecting bag is of substantially the same design as in the embodiment described in connection with FIGS. 1 to 5. Elements having the same or analogous function as in this embodiment bear reference numerals where 400 has been added to the reference numerals of this previous embodiment. Only the elements relevant to the closure device of the collecting bag will be described in detail.

As in the first embodiment, the first closure means is provided in the form of a first pair of contact surfaces 410,411. One of the contact surfaces 410 is provided on a carrier plate 415 extending between a first folding line 412 and a second folding line 413 and is partly covered by a layer of adhesive 416 which may be of the same type as mentioned in connection with the previous embodiments. The other contact surface 411 is provided on another part of the carrier plate 415 and extends from the first folding line 412 to a limiting line 414 situated at a distance from the discharge opening 409. In order to ease the folding operation, the carrier plate 415 is provided with a notch 432 substantially extending along the first folding line 412, or the contact surfaces 410,411 may be provided on separate carrier plates with a spacing between them. As described in connection with the previous embodiments, the size, position and strength of the layer of adhesive 416 may vary, just as a cover layer may be used. Furthermore, the layer of adhesive could as well be provided on the other contact surface 411 or on both of the surfaces 410,411.

On the extension 403a, the back film blank 403 is provided with a carrier plate 435b and the front film blank 402 is at its end portion provided with a similar carrier plate 435b. The carrier plates 435b,435b may be made of a suitable material.

The second closure means comprises one contact surface 418 of a second pair provided in the transition between the discharge portion 408 and the bag member 401. The contact surface 418 is provided with a layer of adhesive 422 intended for adhesive contact with the other contact surface 419 on the opposite film blank.

When closing the collecting bag 401, the discharge portion 408 is first folded along the first folding line 412 thus activating the first closure means 410,411. Subsequently, the discharge portion 408 is folded starting from the distal end by folding the carrier plate 435b against the carrier plate 435b and continue folding until the contact surface 419 has been brought into contact with the contact surface 418 and the second closure means has been activated. By using carrier plates 435b, 435b made from a resilient material, eg., foam, the folding of the discharge portion 408 at the discharge opening 409 provides for an improved tightness. Due to the compressibility of the foam material in combination with the squeezing effect from the film material, particles present in the discharge portion are prevented from moving towards the discharge opening, as described in further detail in applicant's co-pending patent application incorporated herein by reference.

Following this operation, the flap 425 is folded along a third folding line 421 and the contact surface 426 covered by a layer of adhesive 428 is brought into contact with the other surface 427 of the third pair of contact surfaces and the position of use shown in FIGS. 29 and 30 is obtained. As shown in FIG. 27, the adhesive layers 422 and 428 may be formed integrally on a carrier plate 430 extending throughout the flap element and which may be made from foam, plastic or fiber material. In order to facilitate the lifting of the flap 425, the adhesive layers 422 and 428 may be partly covered by cover layers 423, 429 and 431.

In order to open the bag, the flap 425 is lifted and unfolded, following which the second closure means is deactivated. The discharge portion 408 may now be unfolded until an intermediate position has been reached. By a pull in the distal end of the discharge portion 408, the bag is brought to its open or discharge position and the contents of the bag are allowed to flow out through the discharge opening 409.

The invention should not be regarded as being limited to the embodiments described in the above but various modifications and combinations of the shown embodiments may be carried out without departing from the scope of the following claims.

For example, although the invention has been described only with reference to ostomy bags, it is of course possible to apply it to other forms of collecting bags for human body wastes, such as urinal bags or drainage bags for use in connection with surgery.

What is claimed is:

1. A collecting bag for human body wastes comprising:
   a bag member formed by first and second film blanks with joined edges,
   an inlet opening provided in said first film blank,
   connecting elements surrounding said inlet opening for connection of the bag to a body orifice,
   a narrowed, elongated discharge portion starting at a proximal end at a distance from the inlet opening and extending between two end sections of said film blanks to a distal end,
   a discharge opening formed in said discharge portion in a vicinity of said distal end, and
   a closure device being provided for bringing the discharge portion from an open discharge position to a closed position of use, the closure device comprising a first and a second closure means, both of which are activated in said closed position of use,
   said closure device arranged for opening and closing of the bag by successive operation of said first and second closure means in two distinct stages,
   said first closure means comprising first and second predefined contact surfaces constituting a first pair of contact surfaces, said first pair of contact surfaces provided on a carrier plate fastened to one of the film blanks, said first contact surface extending between a first folding line defined by said carrier plate and a second folding line, and said second contact surface extending between the first folding line and a limiting line that defines a second edge of said second contact surface, said first and second contact surfaces being brought into contact with one another by folding the discharge portion along said first folding line and held against one another in the closed position of use.

2. The collecting bag as claimed in claim 1, wherein at least one of the first and second contact surfaces of said first pair includes a layer of adhesive capable of repeated adhesion.

3. The collecting bag as claimed in claim 1, wherein the first closure means is provided at the proximal end of the discharge portion.

4. The collecting bag as claimed in claim 1, wherein the first closure means is provided in the vicinity of the distal end of the discharge portion.

5. The collecting bag as claimed in claim 1, wherein the second closure means includes third and fourth predefined contact surfaces constituting a second pair of contact surfaces, said third and fourth contact surfaces being brought into contact with one another and held against one another in the closed position of use of the bag, and at least one of said third and fourth contact surfaces of said second pair being provided on a carrier plate.

6. The collecting bag as claimed in claim 5, wherein at least one of said third and fourth contact surfaces of said second pair includes a layer of adhesive capable of repeated adhesion.

7. The collecting bag as claimed in claim 3, wherein the second closure means comprises third and fourth predefined contact surfaces constituting a second pair of contact surfaces, said third and fourth contact surfaces being brought into contact with one another and held against one another in the closed position of use of the bag, and at least said third contact surface of said second pair being provided on a carrier plate connected to one of the film blanks at a distance from the discharge portion, and the fourth contact surface being provided at the distal end of the discharge portion.

8. The collecting bag as claimed in claim 7, wherein at least said third contact surface of said second pair includes a layer of adhesive capable of repeated adhesion.

9. The collecting bag as claimed in claim 7, wherein the fourth contact surface of said second pair is provided on an extension of the film blank opposite the film blank carrying said third contact surface.

10. The collecting bag as claimed in claim 9, wherein a supporting film element is provided on the side of said film extension facing away from said fourth contact surface of said second pair, said supporting film element substantially corresponding to a shape and size of said third contact surface of said second pair.

11. The collecting bag as claimed in claim 7, wherein the fourth contact surface of said second pair at least partly is provided on the same film blank as said third contact surface of said second pair at an end zone thereof, and a flap is provided in connection with said third contact surface of said second pair, said flap being foldable along a third folding line and being provided with a layer of adhesive capable of repeated adhesion and constituting a fifth contact surface, a sixth contact surface being provided on the opposite film blank of the discharge portion, said fifth and sixth contact surfaces constituting a third pair of contact surfaces.

12. The collecting bag as claimed in claim 11, wherein the sixth contact surface of said third pair is provided opposite the fourth contact surface of said second pair.

13. The collecting bag as claimed in claim 11, wherein the sixth contact surface of said third pair is provided opposite the first contact surface of said first pair situated between the first and second folding lines, and said flap has a length substantially corresponding to a distance between the third folding line and the proximal end of the discharge portion, the discharge portion being folded on to the bag member along the second folding line and the limiting line in the closed position of use of the bag.

14. The collecting bag as claimed in claim 11, wherein the discharge portion has a length between the first folding line and the distal end which exceeds a distance between the first folding line and the third folding line, the discharge portion being folded along the third folding line in the closed position of use of the bag.

15. The collecting bag as claimed in claim 4, wherein the second closure means includes third and fourth predefined contact surfaces constituting a second pair of contact surfaces, said third and fourth contact surfaces being brought into contact with one another and held against one another in the closed position of use of the bag, and at least said third contact surface of said second pair being provided on a carrier plate, and wherein said third contact surface of said second pair is provided at the proximal end of the discharge portion or at a section of the bag member adjacent the discharge portion.

16. The collecting bag as claimed in claim 15, wherein at least said third contact surface of said second pair includes a layer of adhesive capable of repeated adhesion.

17. The collecting bag as claimed in claim 15, wherein the fourth contact surface of said second pair is provided on the film blank opposite the film blank carrying said third contact surface of said second pair.

18. The collecting bag as claimed in claim 17, wherein a flap is provided in connection with said third contact surface of said second pair, said flap being foldable along a third folding line and being provided with a layer of adhesive capable of repeated adhesion and constituting a fifth contact surface, a sixth contact surface being provided on the opposite film blank of the discharge portion adjacent the fourth contact surface of said second pair, said fifth and sixth contact surfaces constituting a third pair of contact surfaces.

19. The collecting bag as claimed in claim 3, wherein the second closure means includes third and fourth predefined contact surfaces constituting a second pair of contact surfaces, said third and fourth contact surfaces being brought into contact with one another and held against one another in the closed position of use of the bag, and at least said third contact surface of said second pair being provided on a carrier plate, and wherein said third contact surface of said second pair is provided at the proximal end of the discharge portion or at a section of the bag member adjacent the discharge portion.

20. The collecting bag as claimed in claim 19, wherein at least said third contact surface of said second pair includes a layer of adhesive capable of repeated adhesion.

21. The collecting bag as claimed in claim 19, wherein the fourth contact surface of said second pair is provided on the film blank opposite the film blank carrying said third contact surface of said second pair.

22. The collecting bag as claimed in claim 21, wherein a flap is provided in connection with said third contact surface of said second pair, said flap being foldable along a third folding line and being provided with a layer of adhesive capable of repeated adhesion and constituting a fifth contact surface, a sixth contact surface being provided on the opposite film blank of the discharge portion adjacent the fourth contact surface of said second pair, said fifth and sixth contact surfaces constituting a third pair of contact surfaces.

23. The collecting bag as claimed in claim 1, wherein each of said first and second contact surfaces of said first pair is provided on a separate carrier plate, the carrier plates being arranged with a spacing between them which defines the first folding line.

24. The collecting bag as claimed in claim 1, wherein said first pair of contact surfaces is provided on a common carrier plate.

25. The collecting bag as claimed in claim 24, wherein the common carrier plate is provided with a notch along said first folding line.

26. The collecting bag as claimed in claim 1, wherein a supporting plate is fastened to said second film blank opposite said carrier plate.

27. The collecting bag as claimed in claim 26, wherein the supporting plate is provided with a notch opposite said first folding line.

28. The collecting bag as claimed in claim 1, wherein the carrier plate is made from a foam, a plastic or a fiber material.

29. The collecting bag as claimed in claim 2, wherein said layer or layers of adhesive are washable.

30. A collecting bag for human body wastes comprising:
a bag member formed by first and second film blanks with joined edges,
an inlet opening provided in said first film blank,
connecting elements surrounding said inlet opening for connection of the bag to a body orifice,
a narrowed, elongated discharge portion starting at a proximal end at a distance from the inlet opening and extending between two end sections of said film blanks to a distal end,
a discharge opening formed in said discharge portion adjacent said distal end, and
a closure for bringing the discharge portion from an open discharge position to a closed position of use, said closure including first and second predefined contact surfaces provided on a carrier plate fastened to one of the film blanks, said first contact surface extending between a first folding line defined by said carrier plate and a second folding line, and said second contact surface extending between the first folding line and a limiting line that defines a second edge of said second contact surface, said first and second contact surfaces being brought into contact with one another by folding the discharge portion along said first folding line and held against one another in the closed position of use.

31. The collecting bag as set forth in claim 30, wherein said closure further includes a third contact surface provided on a carrier plate connected to one of the film blanks at a distance from the discharge portion, and a fourth contact surface provided at the distal end of the discharge portion, said third and fourth contact surfaces being brought into contact with and held against one another in the closed position of use of the bag.

32. The collecting bag as set forth in claim 31, wherein said fourth contact surface is at least partly provided on a same film blank as said third contact surface, and said closure further includes a flap provided in connection with said third contact surface which is foldable along a third folding line, an underside of said flap constituting a fifth contact surface, a sixth contact surface being provided on an opposite film blank of the discharge portion, said fifth and sixth contact surfaces being brought into contact with and held against one another in the closed position of use of the bag.

* * * * *